(12) United States Patent
Burg et al.

(10) Patent No.: US 9,162,026 B2
(45) Date of Patent: Oct. 20, 2015

(54) INJECTOR SYSTEM

(75) Inventors: Matthias Burg, Berlin (DE); Klaus Urich, Berlin (DE)

(73) Assignee: Bayer Intellectual Property GMBH, Monheim (DE)

( * ) Notice: Subject to any disclaimer, the term of this patent is extended or adjusted under 35 U.S.C. 154(b) by 145 days.

(21) Appl. No.: 13/512,548

(22) PCT Filed: Nov. 24, 2010

(86) PCT No.: PCT/EP2010/068100
§ 371 (c)(1),
(2), (4) Date: Aug. 6, 2012

(87) PCT Pub. No.: WO2011/064243
PCT Pub. Date: Jun. 3, 2011

(65) Prior Publication Data
US 2012/0316435 A1    Dec. 13, 2012

(30) Foreign Application Priority Data
Nov. 27, 2009  (EP) .................................... 09177343

(51) Int. Cl.
*A61M 5/142* (2006.01)
*A61M 5/168* (2006.01)
*G06F 19/00* (2011.01)

(52) U.S. Cl.
CPC ....... *A61M 5/14212* (2013.01); *A61M 5/16827* (2013.01); *G06F 19/3468* (2013.01); *A61M 2205/6018* (2013.01); *A61M 2205/6054* (2013.01)

(58) Field of Classification Search
CPC ..................... A61M 5/14212; A61M 5/16827; A61M 2205/6018; A61M 2205/6054; G06F 19/3468
USPC .......... 604/151, 189, 207–211, 232; 700/213, 700/215, 221, 224–225, 231; 705/2
See application file for complete search history.

(56) References Cited

U.S. PATENT DOCUMENTS 4,966,579 A * 10/1990 Polaschegg .................... 604/65
6,673,033 B1   1/2004 Sciulli et al.
(Continued)

FOREIGN PATENT DOCUMENTS

JP    2007-014463    1/2007
WO   2004091688 A2  10/2004
(Continued)

OTHER PUBLICATIONS

International Search Report and Written Opinion for counterpart International Patent Application No. PCT/EP2010/068100 mailed on May 8, 2011.
(Continued)

*Primary Examiner* — Manuel Mendez
(74) *Attorney, Agent, or Firm* — Joseph L. Kent; David Schramm; James Stevenson

(57) ABSTRACT

The present disclosure relates to a pump injector containing a processor, a pump or a motor with advance for a piston which is suitable for driving liquid out of a container or a cartridge, a data storage device, and a device for data transfer, wherein the processor is electronically connected to the data storage device, to a control unit for the pump or motor, and to the device for data transfer. The injector is suitable for being connected to a container or a cartridge for fluid transfer, which contains a multiplicity of doses of a parenteral solution and has an additional data storage device fixedly connected thereto. The device for data transfer is suitable for reading out information from the additional data storage device on the container including at least one specification in respect to the identity of the product stored in the container or in the cartridge is stored in the container, a maximum dose per patient, and a maximum usage period after opening the container.

20 Claims, 3 Drawing Sheets

(56) References Cited

U.S. PATENT DOCUMENTS

| | | |
|---|---|---|
| 2002/0038392 A1 | 3/2002 | De La Huerga |
| 2005/0119604 A1* | 6/2005 | Bonney et al. ................ 604/19 |

FOREIGN PATENT DOCUMENTS

| | | |
|---|---|---|
| WO | 2006098960 | 9/2006 |
| WO | 2006108026 | 10/2006 |

OTHER PUBLICATIONS

International Preliminary Report on Patentability and Written Opinion for counterpart International Patent Application No. PCT/EP2010/068100 issued on Jun. 5, 2012.

* cited by examiner

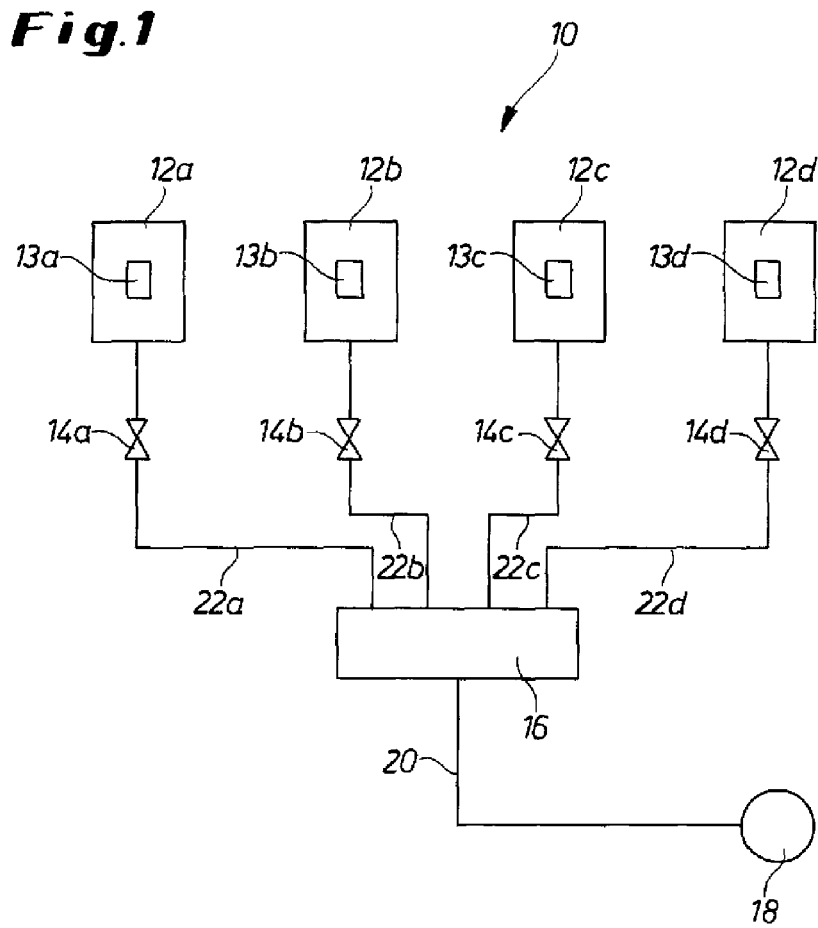

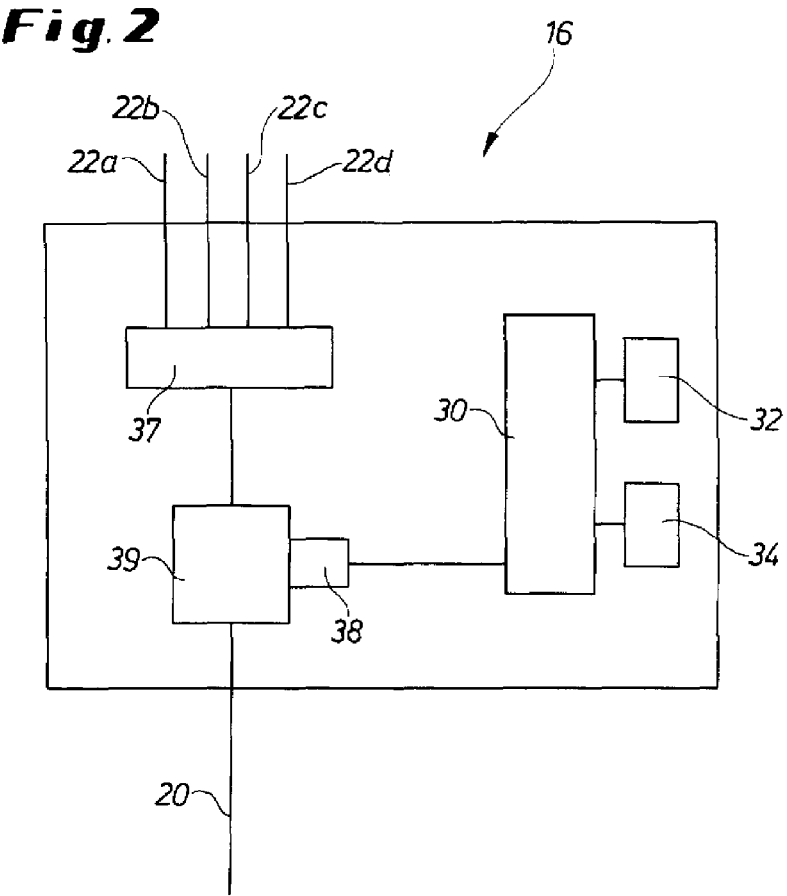

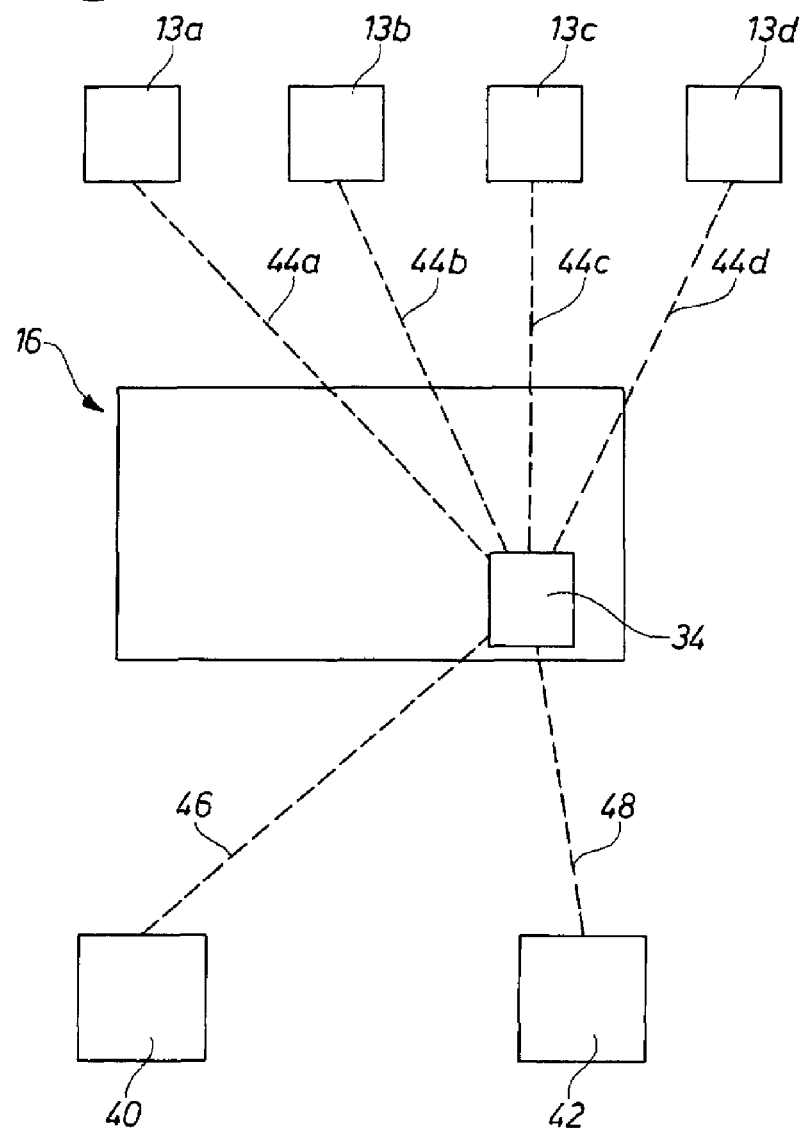

INJECTOR SYSTEM

This application is the U.S. National Phase of International Patent Application No. PCT/EP2010/068100, entitled "Injector System", filed Nov. 24, 2010, which claims priority to European Patent Application No. 09177343.2, filed Nov. 27, 2009, the disclosures of which are incorporated herein by reference in their entirety.

The present disclosure relates to an injector for intravenous and intra-arterial application of parenteral solutions from containers that contain a multiplicity of individual doses of the parenteral solution.

Cartridge injectors are known, which apply individual doses from cartridges and these cartridges are either empty and are to be filled by the user from single or multi-dose containers with the parenteral solution (WO2004/091688A2), or the cartridges are already pre-filled with the parenteral solution (U.S. Pat. No. 6,673,033 B1).

Furthermore, pump injectors are known for removing solutions from containers, which contain a multiplicity of doses of a parenteral solution (multi-use container), and for transferring the removed solution to the patient. By way of example, these injectors are operated by a peristaltic pump and operate as continuous flow systems.

Furthermore, cartridges with a radiofrequency identification (RFID) chip are known. The RFID chip has an electronic data storage device and thereby enables reading out information with the aid of a reader. The RFID chip is used to transfer information from the cartridge to an injector. Transferred information includes information such as the product name, amount specifications, batch number, expiry date of the cartridge, and pressure limit during the removal from the cartridge.

The problem of known injectors consists of the users running the risk of applying too large of a dose of the solution if a container is used that contains a multiplicity of doses of a parenteral solution, or from large cartridges that contain a plurality of doses, since there is no restriction by the defined maximum filling volume like in the single-dose cartridge. Furthermore, there is the risk of using the container or the large cartridge after the first removal for a longer period of time than can be justified for microbiological reasons because there is still solution in the container or the large cartridge once the maximum justified usage duration, which is also specified by the manufacturer, has passed after opening.

There is no automatic documentation of the relevant product and injection protocol parameters (including capture of the opening time of multi-dose containers) because these would usually have to be captured manually (error source, resource limitations) and then more often than not in different systems.

The solution of the specified object consists of the injector described below. The injector can be a pump injector or a cartridge injector for large cartridges. The term "multi-dose container" below comprises all types of containers, bottles or bags. The term "large cartridge" denotes a cartridge or large bottle that is emptied by piston pressure and contains a plurality of doses of a liquid to be applied.

The injector according to the present disclosure is suitable for being connected to one or more multi-dose containers for fluid transfer. Known connections for liquids (e.g. tube connections) can be used to connect the pump injector first to the one or more multi-dose containers and, secondly, to a patient. In the case of the cartridge injector, the output of the cartridge is connected to a patient via known connections for liquids (e.g. tube connections). On the patient side, the connection can for example open into a venous catheter.

Using the injector according to the present disclosure, parenteral solution can be removed from respectively one or more multi-dose containers or large cartridges, and injected individually or, optionally, in parallel.

The multi-dose containers or large cartridges contain parenteral solutions that are applied to the patient. Each multi-dose container or large cartridge contains a multiplicity of doses for being applied to a multiplicity of patients. A container data storage device that can be read wirelessly or via a cable connection (READ function) is fixedly connected to each multi-dose container or to each large cartridge. The container data storage device can optionally also be written to in the same manner (WRITE function). The container data storage device may be a radiofrequency identification (RFID) chip. Other types of optical and/or electronic data storage devices, e.g. one-dimensional codes (bar codes), 2D codes (data matrix) or holographic storage devices, are likewise suitable as a container data storage device. At least specifications relating to the identity of the product situated in the multi-dose container or the large cartridge are stored in the container data storage device. In addition to these specifications in respect of the identity of the product, it is possible to assign product data, or other relevant data stored in other data storage devices, to the multi-dose container or the large cartridge with the corresponding container data storage device.

In addition to the specifications relating to the identity of the product, further information can also be stored in the container data storage device, for example product specific information such as batch number, maximum individual dose and maximum usage period after opening the container, expiry date or filling volume.

The multi-dose containers or large cartridges contain parenteral solutions that are suitable for the examination, preferably a salt solution or a contrast agent.

The pump injector has at least one processor, one pump, one injector data storage device and one device for data transfer. The processor is electronically connected to the injector data storage device, to a control unit for the pump and to the device for data transfer. The device for data transfer is suitable for reading out the data from the container data storage devices.

The cartridge injector has at least one processor, one motor with advance for the piston, which drives the liquid out of the cartridge, one injector data storage device and a device for data transfer. The processor is electronically connected to the injector data storage device, to a control unit for the motor and to the device for data transfer. The device for data transfer is suitable for reading out the data from the container data storage devices.

Information in respect of different products and/or batch numbers can be stored in the injector data storage device. This information includes at least the maximum individual dose and the maximum usage duration after opening the container. Further information available in the injector data storage device can be the batch number, maximum individual dose and maximum usage period after opening the container, expiry date or filling volume.

The device for data transfer of the injector is suitable for reading data from the container data storage device wirelessly or via a cable connection and, optionally, for transmitting data to be stored in the container data storage device using the same method.

When the injector according to the present disclosure is used, the data is transmitted from the container data storage device to the processor of the injector. Either this data already contains specifications in respect of the maximum individual dose and the maximum usage period after opening the container or the processor gathers these specifications from the injector data storage device on the basis of the transmitted specifications in respect of the product identity. The processor of the injector controls the control unit for the pump or the motor such that no more than the maximum individual dose is applied at one time, i.e. without interruption or within a specific period of time, and/or that there is no application from a container or the large cartridge beyond the maximum usage period.

In order to determine the start time for monitoring the maximum usage period, a signal for the processor is triggered either manually by the user or automatically. Automatic triggering of such a signal can be brought about by coupling a multi-dose container or the large cartridge to the injector or by coupling a multi-dose container or the large cartridge to a connection to the injector.

In a further embodiment of the present disclosure, the processor checks whether the utilized multi-dose container or the large cartridge has passed the expiry date. The expiry date is either gathered from the injector data storage device or it is transmitted to the processor from the container data storage device.

The injector can furthermore have a screen, which is likewise connected to the processor. The product information from the injector data storage device or the transmitted product information from the container data storage device can be displayed on the screen. Warning notices when reaching the maximum dose, the maximum usage period or if the expiry date has passed can also be displayed on the screen and/or become audible by means of an acoustic signal.

In a still further embodiment of the present disclosure, the apparatus for data transfer of the injector is suitable for interchanging data wirelessly (radio waves, infrared) or via a cable connection (also e.g. optical waveguides) with further data storage devices. By way of example, these further data storage devices may be associated with a scanner for diagnostic purposes, a database within an apparatus for medically caring for patients or with other systems for logistics, ordering procedures or invoicing services provided.

Information in respect of the injection protocol, or else product-specific information, can be transferred to the further data storage devices from the injector. Information in respect of the injection protocol include, inter alia, type of applied solution, applied solution amount, time/time period of the application, dose, flow rate, maximum pressure during the injection of the solution and scan delay. Product specific information includes, inter alia, product name, concentration, filling volume, batch number, and use-by date.

By means of its device for data transfer, the injector can also receive information from the further data storage devices.

The information transferred by the injector can be used for further electronic data processing in the following manner:
 a) storing the information together with the image data from the examination using a scanner for diagnostic purposes of a patient in e.g. a radiology information system (RIS)
 b) transmitting the information to a hospital information system (HIS) for storing the use in a patient record, ordering/inventory management or an accounting system
 c) balancing risk factors stored in the HIS or RIS with the selected injection parameters before the injection is started. This balancing can be brought about by a processor at the scanner for diagnostic purposes or else by the processor of the pump injector.

FIGURES AND EXAMPLES

FIG. 1 Pump injector system
FIG. 2 Pump injector
FIG. 3 Data transfer between pump injector, container data storage device and further systems FIG. 1 shows a pump injector system 10. A plurality of multi-dose containers 12a to 12d are connected to the pump injector 16 via known tube connections 22a to 22d. Valves 14a to 14d can be used to open or close the tube connections 22a to 22d between the multi-dose containers 12a to 12d and the pump injector 16. On the output side, the pump injector 16 is connected to a venous catheter 18 on the patient via a further tube connection 20. A container data storage device 13a to 13d, which can be read out by a data transfer apparatus on the pump injector 16, is attached to each multi-dose container 12a to 12d.

FIG. 2 shows the pump injector 16. The pump injector 16 contains a processor 30, which is electronically connected to an injector data storage device 32, to a control unit 38 for a pump 39 and to a device for data transfer 34. The device for data transfer 34 is suitable for reading out the data from the container data storage devices 13a to 13d. The tube connections 22a to 22d are connected on the input side to the distributor 37. The tube connection 20 leads from the output side of the distributor 37 to the patient via the pump 39.

FIG. 3 shows the data transfer between pump injector 16, the container data storage devices 13a to 13d, a scanner for diagnostic purposes 40 and the database 42 of a hospital information system (HIS) or a similar system. There is preferably wireless data transfer 44a to 44d between the container data storage devices 13a to 13d and the apparatus for data transfer 34 of the pump injector 16. There can be wireless data transfer 46 between the apparatus for data transfer 34 of the pump injector and the scanner for diagnostic purposes 40 or this data transfer can be brought about by a cable connection, e.g. infrared or optical waveguide. There can be wireless data transfer 48 between the apparatus for data transfer 34 of the pump injector and the database 42 of a HIS or this data transfer can be brought about via a cable connection.

The invention claimed is:

1. A pump injector comprising:
  a processor;
  a pump or a motor with advance for a piston suitable for driving liquid out of a container or a cartridge;
  a data storage device; and
  a device for data transfer,
  wherein the processor is electronically connected to the data storage device, to a control unit for the pump or the motor, and to the device for data transfer,
  wherein the pump injector is suitable for being connected to one or more containers or one or more cartridges for fluid transfer, wherein the one or more containers or the one or more cartridges each contain a multiplicity of doses of a parenteral solution for a plurality of patients,
  wherein an additional data storage device is fixedly connected to the container or the cartridge, and wherein the additional data storage device connected to the container or the cartridge stores information selected from at least one of a maximum individual dose per patient and a maximum usage period after opening the container or the cartridge,
  wherein the device for data transfer is suitable for reading out the information selected from at least one of the maximum individual dose and the maximum usage period after opening the container or the cartridge, from the additional data storage device on the container or the cartridge, and wherein the processor is adapted to control the control unit for the pump or the motor such that not more than the maximum individual dose is injected or that there is no injection from the container or the cartridge beyond the maximum usage period.

2. The pump injector of claim 1, wherein the pump injector is suitable for being connected to a plurality of containers or cartridges for fluid transfer and each comprising the additional data storage device, wherein the plurality of containers or cartridges each respectively contain a multiplicity of doses of a parenteral solution and where the additional data storage device is fixedly connected to each container or cartridge.

3. The pump injector of claim 1, wherein the fluid transfer between the one or more containers or the one or more cartridges and the pump injector takes place via tube connections.

4. The pump injector of claim 1, wherein the fluid transfer between the pump injector and the patient takes place via tube connections and a venous catheter.

5. The pump injector of claim 1, wherein the device for data transfer and the additional data storage device are configured such that information can be stored in the additional data storage device on the one or more containers or on the one or more cartridges via the device for data transfer.

6. The pump injector of claim 1, wherein the device for data transfer and the additional data storage device on the one or more containers or on the one or more cartridges are suitable for wireless interchange of information.

7. The pump injector of claim 1, wherein the additional data storage device on the one or more containers or on the one or more cartridges is a radiofrequency identification (RFID) chip.

8. The pump injector of claim 1, wherein the one or more containers or the one or more cartridges contain either a salt solution or a contrast agent.

9. The pump injector of claim 1, wherein one or more additional items of information are stored in the additional data storage device on the one or more containers or on the one or more cartridges, wherein the one or more additional items of information are selected from the group consisting of a batch number, an expiry date, and a filling volume.

10. The pump injector of claim 1, wherein one or more additional items of information are stored in the data storage device of the pump injector, in conjunction with a specification in respect to an identity of a product, wherein the one or more items of additional information are selected from the group consisting of a batch number, an expiry date, and a filling volume.

11. The pump injector of claim 1, wherein the pump injector further comprises a display screen connected to the processor.

12. The pump injector of claim 1, wherein at least one of the one or more containers or at least one of the one or more cartridges is connected to the pump injector for the purpose of fluid transfer.

13. A container or a cartridge, which contains a multiplicity of doses of a parenteral solution for a plurality of patients, the container or the cartridge comprising:
a data storage device fixedly connected to the container or the cartridge,
wherein the data storage device connected to the container or the cartridge stores information selected from the group consisting of a maximum individual dose per patient, a maximum usage periods after opening the container or cartridge, and combinations thereof.

14. The container or the cartridge of claim 13, wherein the data storage device is an RFID chip or data is available in the form of printed one-dimensional codes, 2D codes, or a hologram.

15. A data interchange system comprising:
a pump injector as recited in claim 1;
one or more containers or one or more cartridges each containing a multiplicity of doses of a parenteral solution for the plurality of patients; and
an additional data storage device fixedly connected to the container or the cartridge and one or more further data storage devices which are each connected to an additional device for data transfer,
wherein the device for data transfer of the pump injector and the additional device for data transfer connected to each of the one or more further data storage devices are suitable for interchanging information with one another.

16. The data interchange system of claim 15, wherein at least one of the one or more further data storage device belongs to a scanner for diagnostic purposes, to a hospital information system (HIS), to an ordering system, or to an accounting system.

17. The data interchange system of claim 15, wherein data transfer between the device for data transfer of the pump injector and the additional device for data transfer of the one or more further data storage devices is brought about wirelessly or via optical waveguides.

18. A pump injector comprising:
a processor;
a pump or a motor with advance for a piston suitable for driving liquid out of a container or a cartridge;
a data storage device; and
a device for data transfer,
wherein the processor is electronically connected to the data storage device, the device for data transfer, and a control unit for the pump or the motor,
wherein the pump injector is suitable for being connected to one or more containers or one or more cartridges for fluid transfer, wherein the containers or the cartridges each contain a multiplicity of doses of a parenteral solution for a plurality of patients,
wherein an additional data storage device is fixedly connected to the container or the cartridge, and wherein at least one specification regarding an identity of a product stored in the container or in the cartridge is stored on the additional data storage device on the container or the cartridge,
wherein the device for data transfer is suitable for reading out the at least one specification regarding the identity of the product stored in the container or in the cartridge,
wherein the data storage device of the pump injector stores the at least one specification regarding the identity of the product and at least one additional items of information selected from a maximum individual dose per patient and a maximum usage period after opening the container, and
wherein the processor is adapted to control the control unit for the pump or the motor such that not more than the maximum individual dose is injected or that there is no injection from a container or cartridge beyond the maximum usage period.

19. The pump injector of claim 18, wherein the pump injector is suitable for being connected to a plurality of containers or cartridges for fluid transfer and each comprising the additional data storage device, wherein the plurality of containers or cartridges respectively contain a multiplicity of doses of a parenteral solution for a plurality of patients and where the additional data storage device is fixedly connected to each container or cartridge.

20. The pump injector of claim 18, wherein the device for data transfer and the additional data storage device are configured on the one or more containers or on the one or more cartridges such that information can be stored in the additional data storage device on the one or more containers or on the one or more cartridges, via the device for data transfer.

* * * * *